United States Patent
Govari (10) Patent No.: US 11,534,067 B2
(45) Date of Patent: Dec. 27, 2022

(54) LEARNED MONITORING DEVICE CORRECTION

(71) Applicant: Biosense Webster (Israel) Ltd., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 65 days.

(21) Appl. No.: 16/541,772

(22) Filed: Aug. 15, 2019

(65) Prior Publication Data

US 2020/0054214 A1  Feb. 20, 2020

Related U.S. Application Data

(60) Provisional application No. 62/764,990, filed on Aug. 20, 2018.

(51) Int. Cl.
*A61B 5/00* (2006.01)
*H04L 29/06* (2006.01)
(Continued)

(52) U.S. Cl.
CPC .......... *A61B 5/0022* (2013.01); *A61B 5/0006* (2013.01); *H04L 65/80* (2013.01); *H04L 67/12* (2013.01)

(58) Field of Classification Search
CPC ....... A61B 5/0006; A61B 5/0022; A61B 5/01; A61B 5/02055; A61B 5/0402;
(Continued)

(56) References Cited

U.S. PATENT DOCUMENTS 5,995,868 A   11/1999   Dorfmeister et al.
10,165,125 B2   12/2018   Govari et al.
(Continued)

FOREIGN PATENT DOCUMENTS

WO   2015/002940 A2   1/2015

OTHER PUBLICATIONS

Extended European Search Report dated Dec. 11, 2019 for the European Patent Application No. 19192363.0.
(Continued)

*Primary Examiner* — Carl H Layno
*Assistant Examiner* — Jane C Kalinock
(74) *Attorney, Agent, or Firm* — Volpe Koenig (57) ABSTRACT

Methods, apparatus, and systems for medical procedures include a monitoring and processing apparatus that includes a memory configured to store a diagnostic algorithm, a sensor configured to sense a patient data of a first patient, a processor configured to generate a first diagnostic result based on the patient data and the diagnostic algorithm. A local computing device is provided and includes a processor configured to receive the first diagnostic result via a first network, receive a first correction indication that includes a correction of the first diagnostic result and transmit the first correction indication via a second network. A remote computing device may be provided and be configured to generate an updated diagnostic algorithm that is updated based on the first correction indication and transmit the updated diagnostic algorithm via the second network.

14 Claims, 8 Drawing Sheets

(51) Int. Cl.
*H04L 29/08* (2006.01)
*H04L 65/80* (2022.01)
*H04L 67/12* (2022.01)

(58) Field of Classification Search
CPC . A61B 5/0476; A61B 5/0488; A61B 5/14503; A61B 5/14532; A61B 5/6802; A61B 5/7475; H04L 65/80; H04L 67/12; G16H 40/63; G16H 50/20; G16H 50/70
USPC ........................................................ 600/300
See application file for complete search history.

(56) References Cited

U.S. PATENT DOCUMENTS

| | | |
|---|---|---|
| 2007/0100278 A1 | 5/2007 | Frei et al. |
| 2007/0179434 A1 | 8/2007 | Weinert et al. |
| 2013/0345663 A1 | 12/2013 | Agrawal et al. |
| 2017/0265765 A1* | 9/2017 | Baumann et al. |
| 2018/0085011 A1* | 3/2018 | Ma ....................... A61B 5/0225 |
| 2019/0336025 A1* | 11/2019 | Qu ....................... G06K 9/0055 |
| 2020/0038671 A1* | 2/2020 | Schulhauser ........ A61B 5/7282 |
| 2020/0330050 A1* | 10/2020 | Peters .................... G16H 40/60 |

OTHER PUBLICATIONS

Stuntebeck et al., "HealthSense: Classification of Health-related Sensor Data through User-Assisted Machine Learning." HotMobile '08 (2008).
Extended European Search Report dated Jan. 15, 2020 for the European Patent Application No. 19192375.4.

* cited by examiner

LEARNED MONITORING DEVICE CORRECTION

CROSS REFERENCE TO RELATED APPLICATION

This application claims the benefit of U.S. provisional application No. 62/764,990 filed on Aug. 20, 2018, which is incorporated by reference as if fully set forth.

FIELD OF INVENTION

The present application provides systems, apparatuses, and methods for improving medical device procedures.

BACKGROUND

Medical monitoring and processing apparatuses that are attached to or implanted within a patient can provide useful information for the diagnosis and treatment of medical conditions experienced by the patient. Such devices may be attached to the surface of a patient's body, such as via an adhesive component. Alternatively, such devices can be internal to a patient's body (e.g., subcutaneously implantable) and may gather data from within the patient's body.

A monitoring and processing apparatuses that is attached to or inserted into a patient may provide data and analysis to external devices, which may further use the data and/or analysis for treatment purposes.

SUMMARY

Methods, apparatus, and systems for medical procedures are disclosed herein and include a monitoring and processing apparatus that includes a memory configured to store a diagnostic algorithm, a sensor configured to sense a patient data of a first patient, a processor configured to generate a first diagnostic result based on the patient data and the diagnostic algorithm. The monitoring and processing apparatus may be an external apparatus or an implantable apparatus. A local computing device is provided and may include a processor and configured to receive the first diagnostic result via a first network, receive a first correction indication that comprises a correction of the first diagnostic result and transmit the first correction indication via a second network. A remote computing device may be provided and be configured to generate an updated diagnostic algorithm that is updated based on the first correction indication and transmit the updated diagnostic algorithm via the second network. The updated diagnostic algorithm may be received by a plurality of second monitoring and processing apparatuses and the plurality of second monitoring and processing apparatuses may be selected based on at least one of a location, a predetermined grouping, or a patient-based grouping.

The updated diagnostic algorithm may be generated based on the first correction indication and a second correction indication. The updated diagnostic algorithm may be updated based on a threshold number of correction indications including the first correction indication and the second correction indication. The second correction indication may be based on a second patient. The diagnostic algorithm may include a first weight and the updated diagnostic algorithm may include an updated first weight.

The monitoring and processing apparatus sensor may configured to sense the patient data using one or more electrodes coupled to the monitoring and processing apparatus. The patient data may include an electrocardiograph (ECG) signal.

The first network may be a local area network (LAN) and the second network is a wide area network (WAN).

Patient data of a first patient may be sensed at a first monitoring and processing apparatus. The monitoring and processing apparatus may be an external apparatus or an implantable apparatus. A first diagnostic result may be generated based on the patient data and a diagnostic algorithm. The first diagnostic result may be transmitted via a first network. An updated diagnostic algorithm may be received from a local computing device via the first network and the updated diagnostic algorithm may be based at least on a first correction indication comprising a correction of the first diagnostic result and provided to the local computing device by a remote computing device via a second a second network. A second diagnostic result may be generated based on the updated diagnostic algorithm.

The updated diagnostic algorithm may be further based on a second correction indication. According to an embodiment, the updated diagnostic algorithm may be updated based on a threshold number of correction indications comprising the first correction indication and the second correction indication. The second correction indication may be based on a second patient. The diagnostic algorithm may include a first weight and the updated diagnostic algorithm may include an updated first weight.

Sensing patient data at the monitoring device may include sensing the patient data using one or more electrodes coupled to the monitoring and processing apparatus. The patient data may include an electrocardiograph (ECG) signal. The first network may be a local area network (LAN) and the second network is a wide area network (WAN).

According to an embodiment, a first monitoring and processing apparatus may include a sensor configured to sense a patient data of a first patient and a transmitter configured to transmit the patient data via a first network. A local computing device may be provided and may include a memory configured to store a diagnostic algorithm and a processor configured to receive the patient data via the first network, generate a first diagnostic result based on the patient data and the diagnostic algorithm, receive a first correction indication that comprises a correction of the first diagnostic result and transmit the first correction indication via a second network. A remote computing device may be provided and may be configured to generate an updated diagnostic algorithm that is updated based on the first correction indication and transmit the updated diagnostic algorithm via the second network.

BRIEF DESCRIPTION OF THE DRAWINGS

A more detailed understanding can be had from the following description, given by way of example in conjunction with the accompanying drawings wherein.

DETAILED DESCRIPTION

According to embodiments of the disclosed subject matter, a monitoring and processing apparatus may be attached to or implanted in a patient, such as a cardiac patient, and may monitor the medical status of a patient. Patient biometrics acquired by the monitoring and processing apparatus, in response to signals generated by the patient (e.g., the patient's heart), and analysis or diagnosis derived from the patient data may be transmitted wirelessly to a local computing device (e.g., a computer or mobile device). The patient biometrics may be analyzed by the monitoring and processing apparatus and/or the local computing device and a diagnostic result may be provided based on the same. A diagnostic result may be determined by using a diagnostic algorithm.

A diagnostic result provided by the diagnostic algorithm may be provided to a healthcare professional via a local computing device. The healthcare professional may determine that the diagnostic result is incorrect, in whole or in part. The healthcare professional may provide a correction indication via the local computing device. For example, the healthcare professional may determine that a cardiac signal has been incorrectly identified by the diagnostic algorithm as indicating atrial fibrillation. The healthcare professional may determine that the cardiac signal indicates atrial tachycardia instead of an atrial fibrillation. Accordingly, the healthcare professional may provide a correction indication that corrects the diagnostic result to be atrial tachycardia instead of an atrial fibrillation.

The correction indication may be provided to a remote computing device that may be configured to receive correction indications from different local computing devices. The remote computing device may determine, based on the correction indication, or a plurality of correction indications, that the diagnostic algorithm should be updated. For example, the remote computing device may determine that one or more weights within the diagnostic algorithm should be updated based on the one or multiple correction indications received by the remote computing devices. The remote computing device may update the diagnostic algorithm, based on the determination, and may provide the updated diagnostic algorithm to one or more local computing devices and/or monitoring and processing apparatuses.

Embodiments described herein provide systems, apparatuses, and methods for remotely monitoring various biometric patient activity (e.g., electrocardiogram (ECG) signals, electroencephalography (EEG) signals, Electromyography (EMG) signals, blood pressure, temperature and other measurable biometrics) for use with different medical modalities (e.g., ECG monitoring, pressure monitoring, orthopedics, and pain management treatment) for treatment across various disease states.

Embodiments described herein include one or more monitoring and processing apparatuses that continuously or periodically monitor the patient biometrics (i.e., patient data) and temporarily store (e.g., in buffer memory) the patient data for a period of time (e.g., 1 hour). Upon detection of an event (e.g., a user input, a detected arrhythmia, a loss of contact or connection), the one or more monitoring and processing apparatuses may store a portion of the patient data at and within a range of time before and after the detected event to non-volatile memory. According to an embodiment, the one or more monitoring and processing apparatuses may analyze the patient data based on a diagnostic algorithm and generate a diagnostic result based on the same. Additionally, the one or more monitoring and processing apparatus may wirelessly communicate, via a short-range network (e.g., local area network (LAN) or personal area network (PAN)), the portion of the patient data to a local computing device in synchronous communication with the monitoring and processing apparatus. The local computing device may display one or more diagnostic results, all or a portion of the patient data, and information associated with the patient data (e.g. additional information from another device, etc.), and communicate, via a long-range network (e.g., wide area network (WAN), the internet, a cellular network), at least some of the patient data, one or more diagnostic results, and the associated information to a remote computing system.

Figure 1:
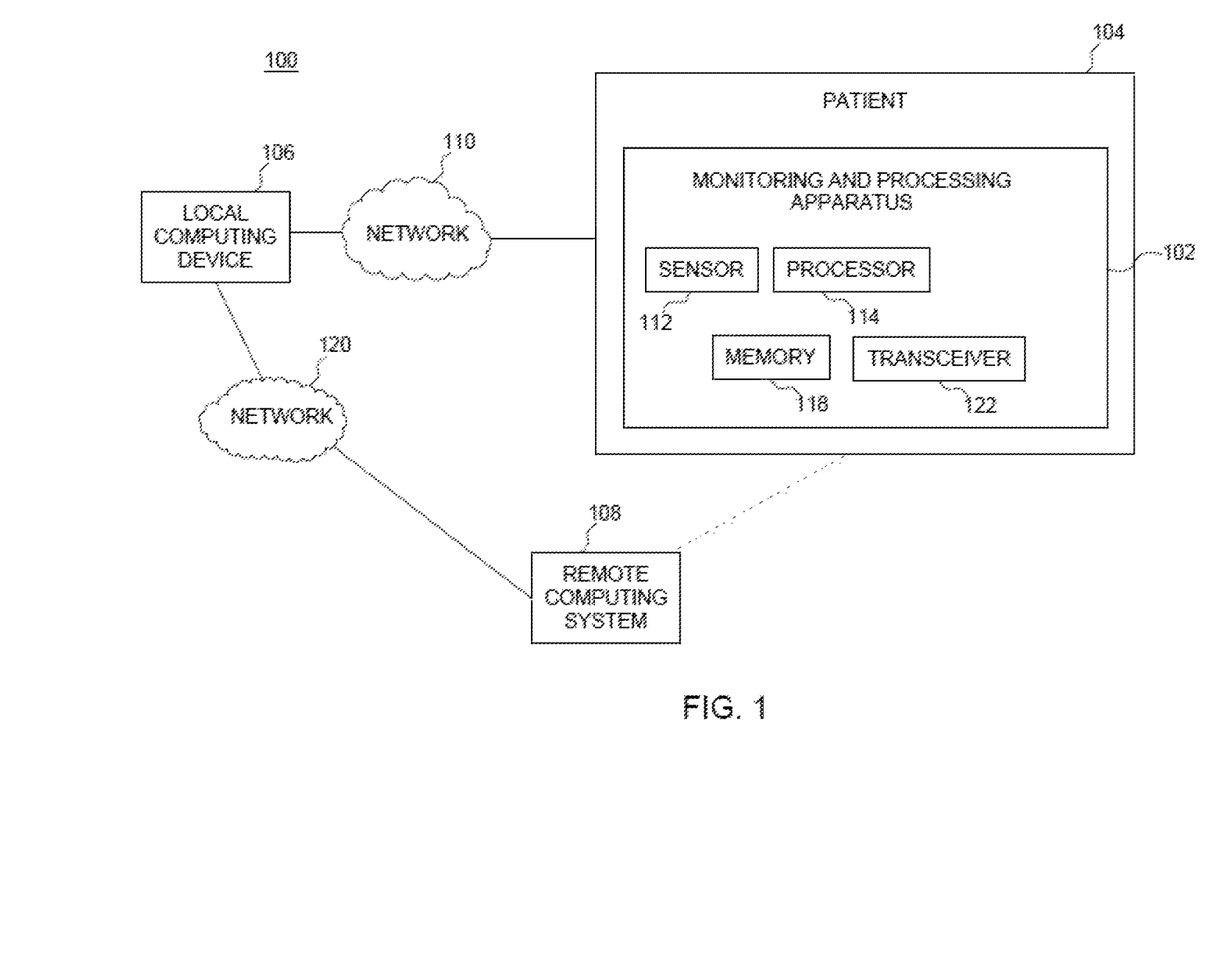
FIG. 1 is a block diagram of an example system for updating a diagnostic algorithm based on correction indications.

FIG. 1 is a block diagram of an example system 100 for updating a diagnostic algorithm based on correction indications. In the example illustrated in FIG. 1, the system 100 includes a patient biometric monitoring and processing apparatus 102 associated with a patient 104, a local computing device 106, a remote computing system 108, a first network 110 and a second network 120.

According to an embodiment, a monitoring and processing apparatus 102 may be an apparatus that is internal to the patient's body (e.g., subcutaneously implantable). The monitoring and processing apparatus 102 may be inserted into a patient via any applicable manner including oral injection, surgical insertion via a vein or artery, an endoscopic procedure, or a laparoscopic procedure.

According to an embodiment, a monitoring and processing apparatus 102 may be an apparatus that is external to the patient. For example, the monitoring and processing apparatus 102 may include an attachable patch (e.g., that attaches to a patient's skin). The monitoring and processing apparatus 102 may also include a blood pressure cuff, a weight scale, a bracelet or smart watch biometric tracker, a glucose monitor, a continuous positive airway pressure (CPAP) machine or virtually any device which may provide an input concerning the health or biometrics of the patient.

According to an embodiment, a monitoring and processing apparatus 102 may include both components that are internal to the patient and components that are external to the patient.

A single monitoring and processing apparatus 102 is shown in FIG. 1. Example systems may, however, include a plurality of patient biometric monitoring and processing apparatuses. A patient biometric monitoring and processing apparatus may be in communication with one or more other patient biometric monitoring and processing apparatuses. Additionally, a monitoring and processing apparatus may be in communication with the network 110.

One or more monitoring and processing apparatuses 102 may acquire patient data (e.g., electrical signals, blood pressure, temperature, blood glucose level or other biometric data) and receive at least a portion of the patient biometric data representing the acquired patient biometrics and additional formation associated with acquired patient biometrics from one or more other monitoring and processing apparatuses 102. The additional information may be, for example, diagnosis information and/or additional information obtained from an additional device such as a wearable device. Each monitoring and processing apparatus 102 may process data, including its own acquired patient data as well as data received from one or more other monitoring and processing apparatuses 102. One or more monitoring and processing apparatus 102 may analyze the patient data based on a diagnostic algorithm stored in a monitoring and processing apparatus 102 memory and provide one or more diagnostic results based on the analysis.

In FIG. 1, network 110 is an example of a short-range network (e.g., local area network (LAN), or personal area network (PAN)). Information may be sent, via short-range network 110, between monitoring and processing apparatus 102 and local computing device 106 using any one of various short-range wireless communication protocols, such as Bluetooth, Wi-Fi, Zigbee, Z-Wave, near field communications (NFC), ultraband, Zigbee, or infrared (IR).

Network 120 may be a wired network, a wireless network or include one or more wired and wireless networks. For example, a network 120 may be a long-range network (e.g., wide area network (WAN), the internet, or a cellular network). Information may be sent, via network 120, using any one of various long-range wireless communication protocols (e.g., TCP/IP, HTTP, 3G, 4G/LTE, or 5G/New Radio).

The patient monitoring and processing apparatus 102 may include a patient biometric sensor 112, a processor 114, a memory 118, and a transmitter-receiver (i.e., transceiver) 122. The patient monitoring and processing apparatus 102 may continually or periodically monitor, store, process and communicate, via network 110, any number of various patient biometrics. The patient data may be monitored and communicated for treatment across any number of various diseases, such as cardiovascular diseases (e.g., arrhythmias, cardiomyopathy, and coronary artery disease) and autoimmune diseases (e.g., type I and type II diabetes).

Patient biometric sensor 112 may include, for example, one more sensors configured to sense patient biometrics. For example, patient biometric sensor 112 may include one or more electrodes configured to acquire electrical signals (e.g., heart signals, brain signals or other bioelectrical signals), a temperature sensor, a blood pressure sensor, a blood glucose sensor, a blood oxygen sensor, a pH sensor, an accelerometer and a microphone). The patient biometric sensor 112 may be powered by a power source (not shown) such as a battery and/or chargeable capacitor that may also supply operating power to other components of the monitoring and processing apparatus 102. The power source may be researchable, for example, by radio-frequency (RF) energy.

According to an example, the monitoring and processing apparatus 102 may be a continuous glucose monitor (CGM) for continuously monitoring blood glucose levels of a patient on a continual basis for treatment of various diseases, such as type I and type II diabetes. The CGM may include a subcutaneously disposed electrode, which may monitor blood glucose levels from interstitial fluid of the patient. The CGM may be, for example, a component of a closed-loop system in which the blood glucose data is sent to an insulin pump for calculated delivery of insulin without user intervention.

Transceiver 122 may include a transmitter and receiver. Alternatively, transceiver 122 may include a transmitter and receiver integrated into a single device. Transceiver 122 may be configured to receive and transmit signals using network 110.

Processor 114 may be configured to store data, such as patient data (e.g., patient biometric data) in memory 118 acquired by patient biometric sensor 112, and communicate the patient data, across network 110, via a transmitter of transceiver 122. Data from one or more other monitoring and processing apparatus 102 may also be received by a receiver of transceiver 122.

The local computing device 106 of system 100 may be in communication with the monitoring and processing apparatus 102 and may be configured to act as a gateway to the remote computing system 108 through the second network 120. The local computing device 106 may be, for example, a smart phone, smartwatch, tablet or other portable smart device configured to communicate with other devices via network. Alternatively, the local computing device 106 may be a stationary or standalone device, such as a stationary base station including, for example, modem and/or router capability, a desktop or laptop computer using an executable program to communicate information between the processing apparatus 102 and the remote computing system 108 via the PC's radio module, or a USB dongle. Patient data may be communicated between the local computing device 106 and the patient biometric monitoring and processing apparatus 102 using a short-range wireless technology. The local computing device 106 may be configured to display the acquired patient data and information, such as diagnostic results, associated with the acquired patient data.

Figure 2:
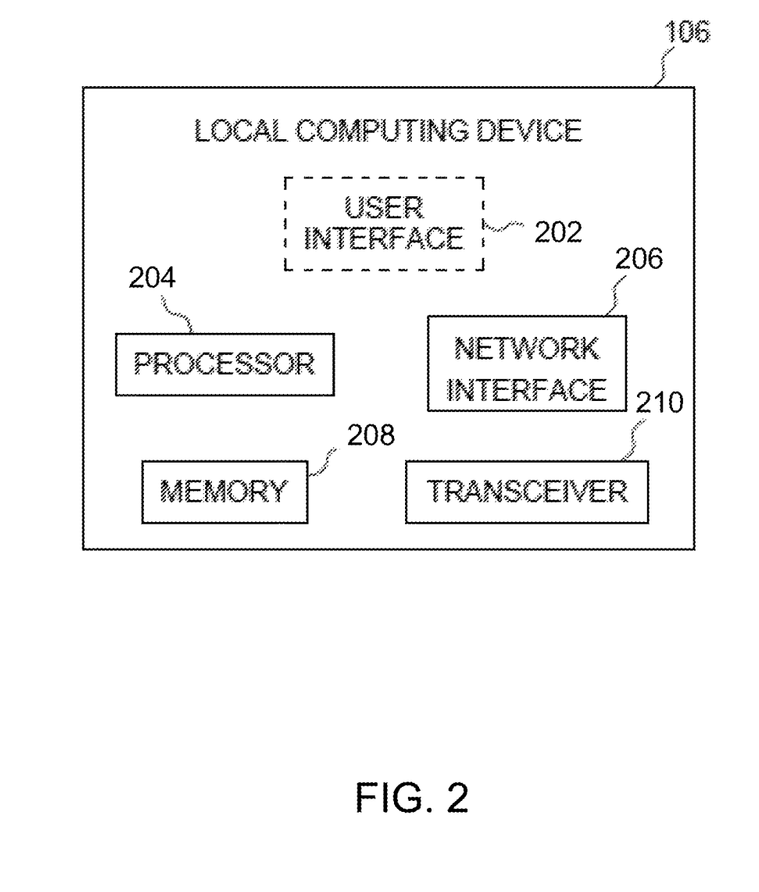
FIG. 2 is a block diagram of an example local computing device.

FIG. 2 is a block diagram of an example of the local computing device 106 of FIG. 1. As described above, the local computing device 106 may be a mobile device (e.g., smart phone, smart watch, tablet or other portable smart device configured to communicate with other devices via network). Alternatively, the local computing device 106 may be a stationary device (e.g., a stationary base station including for example, modem and/or router capability, a desktop or laptop computer or other dedicated standalone device). As shown in FIG. 2, the local computing device 106 may include one or more of a user interface 202, a processor 204, a network interface 206 (e.g., for a mobile device or a stationary device with a network connection), memory 208, and a transceiver 210.

The memory 208 may be configured to store a diagnostic algorithm. The processor 204 may be configured to receive patient data and provide a diagnostic result based on the diagnostic algorithm stored in memory 208. Although a single diagnostic algorithm is described herein, it should be understood that multiple diagnostic algorithms may be stored (e.g., in memory 208) and used (e.g., by processor 204) to provide one or more diagnostic results.

Figure 4:
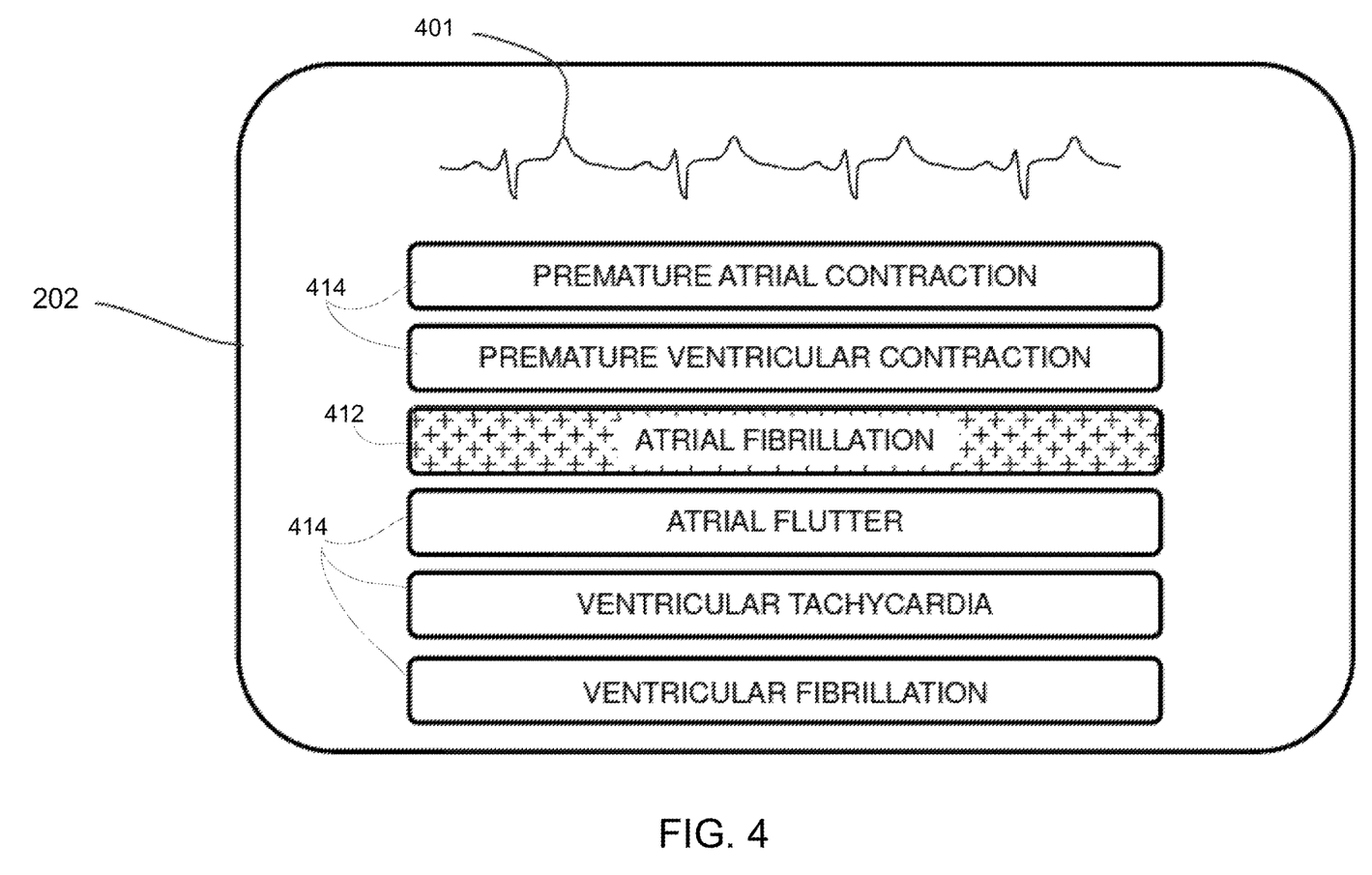
FIG. 4 is a diagram of an example display of a local computing device.

User interface 202 may be, for example, a touch screen configured to display information, such as patient biometrics, diagnostic results and/or receive user inputs. Processor 204 may be configured to control the user interface to execute an application that displays the monitored patient data received from one or more monitoring and processing apparatus 102 of FIG. 1. Alternatively or additionally, processor 204 may also be configured to provide an indication to a sensor 112 of FIG. 1. The indication may be a signal (e.g., activation or wake up signal, activity signal, or inactivity signal), data, or the like. FIG. 4, as further described herein, shows an example user interface 202.

Figure 3A:
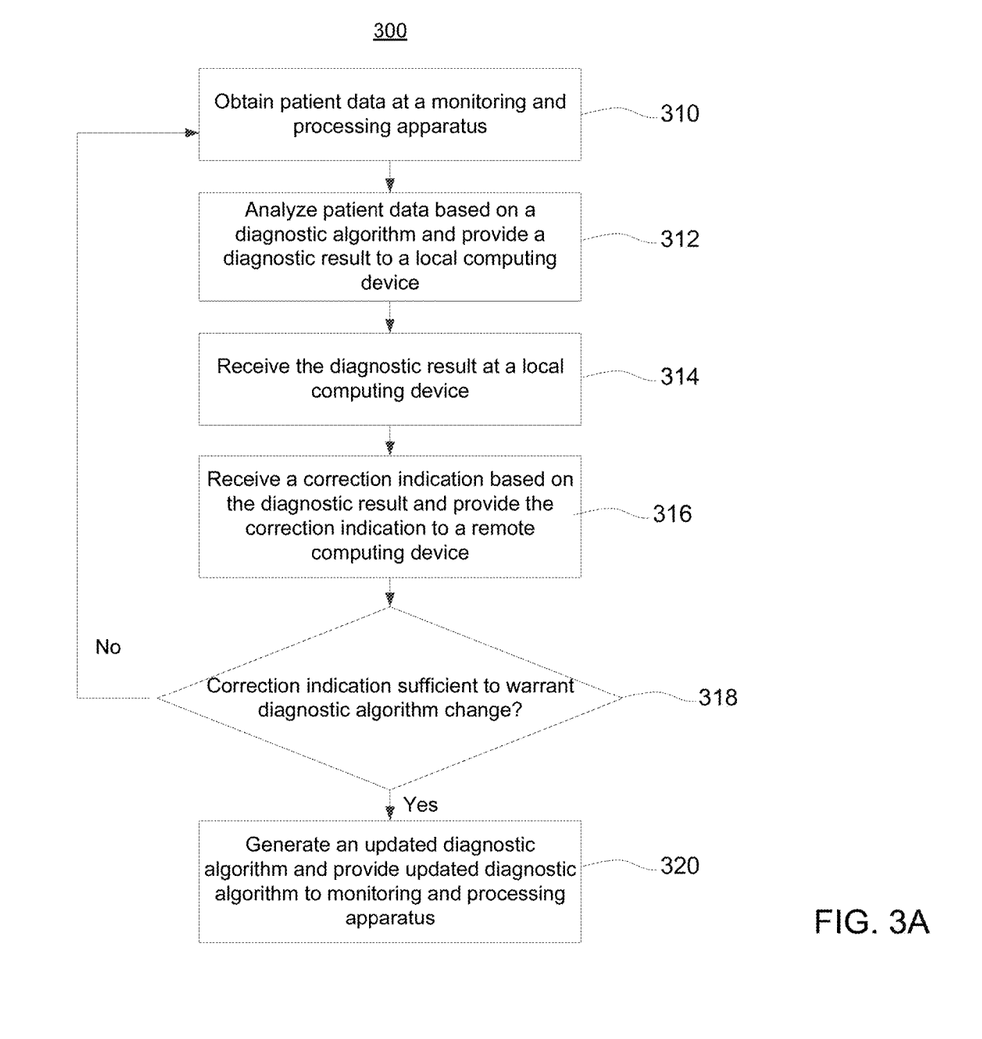
FIG. 3A is a flow chart of an example method of generating an updated diagnostic algorithm.

FIG. 3A is a diagram of an example method 300 of generating an updated diagnostic algorithm. At 310 of method 300, patient data may be obtained at a monitoring and processing apparatus. The monitoring and processing apparatus may be the same as or similar to monitoring and processing apparatus 102 of FIG. 1. The patient data may be obtained by one or more sensors (e.g., sensor 112) configured to sense patient biometric data. The patient data may be sampled continuously or at pre-determined or dynamically determined time intervals. As an example, patient data may be sampled at 5 second intervals. As another example, the frequency of the sampling may be determined based on a patient history such that a higher sampling rate may be utilized for a patient that is more prone to a medical condition and a lower sampling rate may be utilized for a patient that is less prone to a medical condition. The patient data may be stored in a memory, such as memory 118 of FIG. 1.

Figure 7:
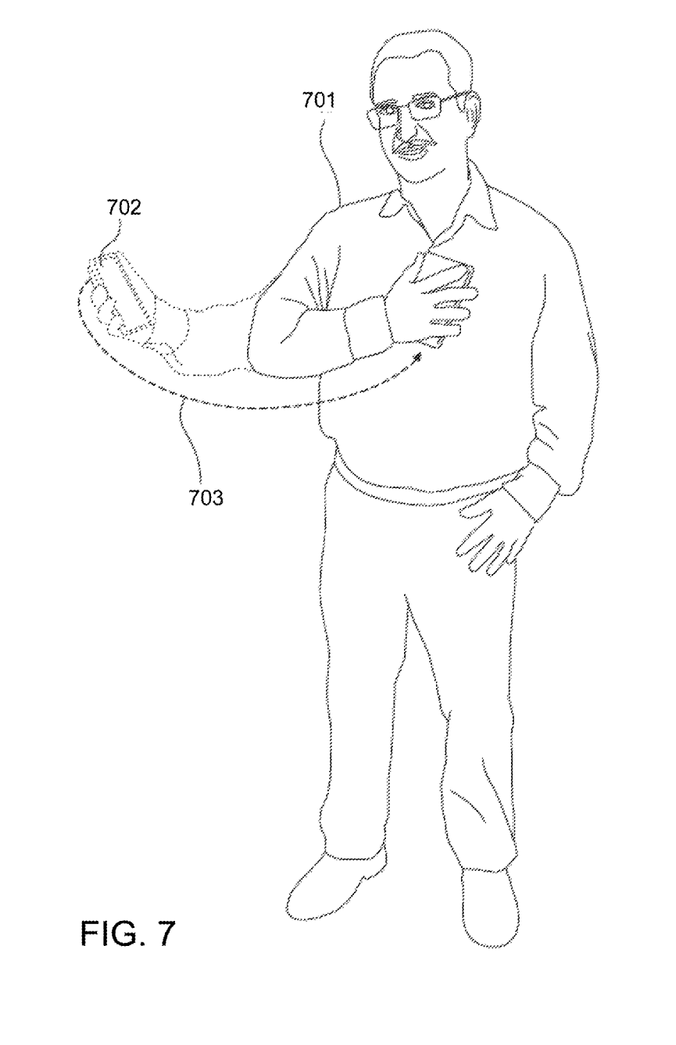
FIG. 7 is a diagram of an example gesture based input.

According to an embodiment, the patient data may be sampled based on a patient input. A patient input may include an input via a local computing device, a voice command, a gesture, or the like. FIG. 7 shows an example of a gesture based patient input where a patient 701 or a caregiver (not shown) may initiate the sampling of patient data by performing a motion 703 using a mobile device 702. The mobile device 702 may include one or more sensors, such as an accelerometer, which may provide an indication that a predetermined gesture is performed. The predetermined gesture may be converted into an input to sample patient data and an input signal may be provided to a monitoring and processing apparatus via network 110 of FIG. 1. Further, the mobile device 702 may be placed in a receive mode and may be configured to receive data from a monitoring and processing apparatus. According to an embodiment, an input signal may be generated by the mobile device 702 based on both the motion 703 as well as the change in proximity of the mobile device 702 to a monitoring and processing apparatus (not shown in FIG. 7).

At 312 of method 300, the patient data may be analyzed at the monitoring and processing apparatus. The patient data may be analyzed by a processor, such as processor 114 of FIG. 1. The processor may analyze the patient data based on a diagnostic algorithm that may be stored in monitoring and processing apparatus memory, such as memory 118.

The processor may analyze the patient data based on the diagnostic algorithm in any applicable format such as by utilizing the patient data as inputs for the diagnostic algorithm and then matching the output of the diagnostic algorithm to pre-determined and/or stored diagnoses. Accordingly, one or more diagnoses that most closely match the output of the diagnostic algorithm may be determined to be the diagnostic result.

Alternatively, the processor may analyze the patient data by comparing the patient data to known data that corresponds to one or more diagnostic results. Accordingly, one or more known data, corresponding to one or more diagnoses that most closely match the patient data may be identified and the one or more diagnoses may be determined to be the diagnostic result.

Figure 5:
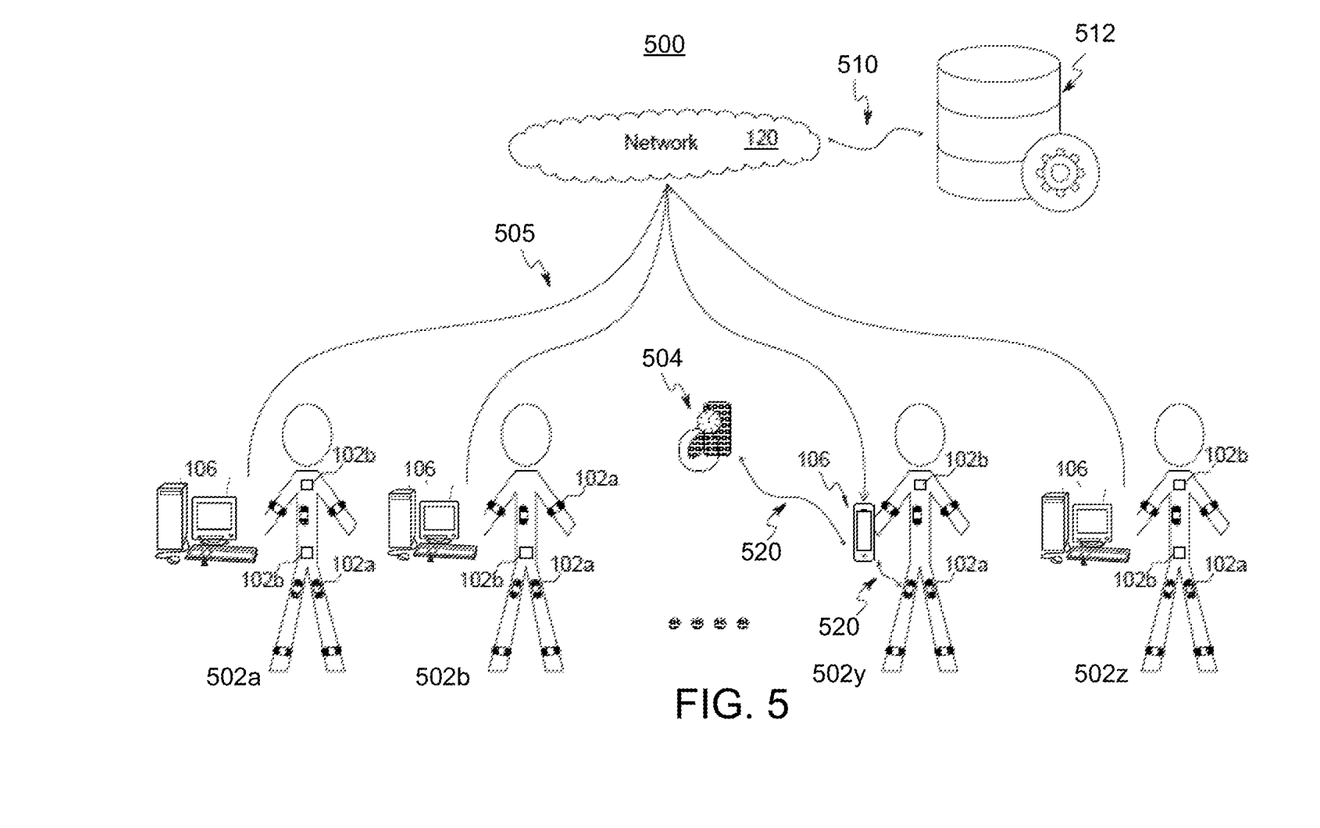
FIG. 5 is a block diagram of an example system for updating a diagnostic algorithm based on correction indications for multiple patients.

According to an embodiment, the processor may receive additional data from an additional device, such as the external sensing apparatus 504 of FIG. 5, as further disclosed herein. As a simplified example, an additional device may be a thermometer that provides patient or environmental temperature readings as additional data. The additional data may be utilized as an input for the diagnostic algorithm.

The diagnostic algorithm may include weights that are configured to enable the diagnostic algorithm to determine a diagnostic result. The weights may enable the diagnostic algorithm to match the patient data to a diagnosis and, accordingly, to provide a diagnostic result. As a simplified example, a monitoring and processing apparatus may include electrodes that sense local activation time (LAT) values of a patient's heart. The diagnostic algorithm may apply a given weight X to LAT values within a first range and a different weight Y to LAT values within a second range. The diagnostic algorithm may then compare the result weighted LAT values to the pre-mapped values of a known diagnosis (e.g., atrial fibrillation) to determine if given patient data corresponds to the known diagnosis. If the weighted LAT values correspond to the pre-mapped values of the known diagnosis, the known diagnosis may be provided as a diagnostic result.

The diagnostic algorithm may be pre-installed and/or stored in the monitoring and processing apparatus memory at a time of manufacturing or prior to the monitoring and processing apparatus being placed on/in a patient. Alternatively, the diagnostic algorithm may be transmitted onto the monitoring and processing apparatus after it is placed on/in the patient.

One or more diagnostic results, as determined by the monitoring and processing apparatus' processor, may be transmitted via a local area network such as network 110 of FIG. 1. At 314 of method 300, the one or more diagnostic results may be received by a local computing device, such as local computing device 106 of FIGS. 1 and 2. According to an embodiment, the diagnostic result may be pushed to the local computing device, via the local area network, upon a determination of the diagnostic result. For example, upon a determination and transmission of the diagnostic result, a notification may be provided on a user interface 202 of the local computing device 106.

According to an embodiment, a diagnostic result may be transmitted to a local computing device based on a patient input. A patient input may include an input via a local computing device, a voice command, a gesture, or the like. FIG. 7 shows an example of a gesture based patient input where a patient 701 or a caregiver (not shown) may initiate the transfer of a diagnostic result by performing a motion 703 using a mobile device 702. The mobile device 702 may include one or more sensors, such as an accelerometer, which may provide an indication that a predetermined gesture is performed. The predetermined gesture may be converted into an input signal to instruct a monitoring and processing apparatus to transmit one or more diagnostic results and an input signal may be provided to a monitoring and processing apparatus via network 110 of FIG. 1. Further, the mobile device 702 may be placed in a receive mode and may be configured to receive data from a monitoring and processing apparatus. According to an embodiment, an input signal may be generated by the mobile device 702 based on both the motion 703 as well as the change in proximity of the mobile device 702 to a monitoring and processing apparatus (not shown in FIG. 7).

A local computing device that receives a diagnostic result may be accessed by a healthcare professional such as a physician or a medical technician. Additionally, the patient data and/or a portion or indication of the patient data may also be received from the monitoring and processing apparatus at the local computing device. FIG. 4 shows an example user interface 202 of a local computing device. Patient data 401 is provided via the user interface 202 and may be displayed along with a diagnostic result 412 as well as one or more alternative diagnoses 414.

At 316 of method 300, the local computing device may receive a correction indication based on a diagnostic result provided at 312. The correction indication may be provided by a healthcare professional or may be automatically determined based on software located at the local computing device. The health care professional or the local computing device software may provide the correction indication based on one or more factors such as, but not limited to, the patient data (e.g., patient data 401 of FIG. 4), patient history, data from an additional device (e.g., a blood pressure cuff, a weight scale, a bracelet or smart watch biometric tracker, a glucose monitor, a CPAP machine or any device which may provide an input concerning the health or biometrics of the patient), and/or patient observation.

The correction indication received at 316 of method 300 may be provided by a touch input, voice command, via an accessory (e.g., keyboard, mouse, etc.), a gesture, or the like. As an example, the correction indication may be provided by selecting one of the diagnoses 414 from the user interface 202 of FIG. 4, using a computer mouse.

As shown at 316 of method 300, the correction indication may be provided to a remote computing device such as remote computing device 106 of FIG. 1. A more detailed description of the remote computing device 106 is provided in FIG. 6. The correction indication may be provided to a remote computing device via a wide area network such as wide area network 120 of FIG. 1.

The remote computing device may be configured to receive correction indications from one or more local computing devices, as further described herein. Further, the diagnostic algorithm or a version of the diagnostic algorithm may be stored at a remote computing device.

At step 318 of process 300, the remote computing device may make a determination whether a received correction indication is sufficient to warrant a change to the diagnostic algorithm. The determination may be made based on one or more factors such as, but not limited to, the source of the correction indication (e.g., a first source may be weighted higher than a second source), the number of similar correction indications received, the frequency of similar correction indications received, the frequency of the corrected diagnostic result, the frequency of correction indication received for the given diagnostic result, a patient population, or a location. The determination may be made based on a predetermined or dynamically determined threshold. For example, if the remote computing device receives a threshold number of correction indications when a first diagnostic result is provided to health care professionals, then 318 may be triggered in the affirmative and 320 may be performed. Continuing the example, if a correction indication does not meet a threshold number of received correction indications, then 318 may not be triggered and the method 300 may cycle back to 310 and patient data may be analyzed based on an existing diagnostic algorithm.

If 318 is triggered in the affirmative, 320 of method 300 may be performed. At 320, an updated diagnostic algorithm may be generated based at least on the correction indication. The updated diagnostic algorithm may include one or more updated weights.

Alternatively, or additionally, the updated diagnostic algorithm may include one or more updated variables such that additional or different portions of the patient data are utilized when determining diagnostic results. An updated variable may be added, for example, based on additional data provided by an external sensing apparatus (e.g., the external sensing apparatus 504 of FIG. 5). As an example, an external sensing apparatus may provide elevation data that provides the sea level recorded when a correction indication is received. A determination may be made that a given correction indication is repeatedly received when the sea level indicated by a plurality of different external sensing apparatus in different locations indicate a sea level above a threshold sea level. Accordingly, an elevation-based variable may be added to a diagnostic algorithm such that if a sea level reading or other elevation data is available, then the elevation-based variable is a factor in determining diagnostic results using the updated diagnostic algorithm.

The updated diagnostic algorithm may be applied such that patent data analyzed based on the updated diagnostic algorithm can provide different results (e.g., diagnostic results) than the results provided by analyzing the same patient data based on the original diagnostic algorithm.

An updated diagnostic algorithm, as generated at 320 of method 300, may be stored at a remote computing device memory. According to an embodiment, the updated diagnostic algorithm may be provided to one or more monitoring and processing devices. The updated diagnostic algorithm may be provided to the monitoring and processing apparatuses when the diagnostic algorithm is updated at 320. Alternatively, the updated diagnostic algorithm may be provided during a software update.

Figure 3B:
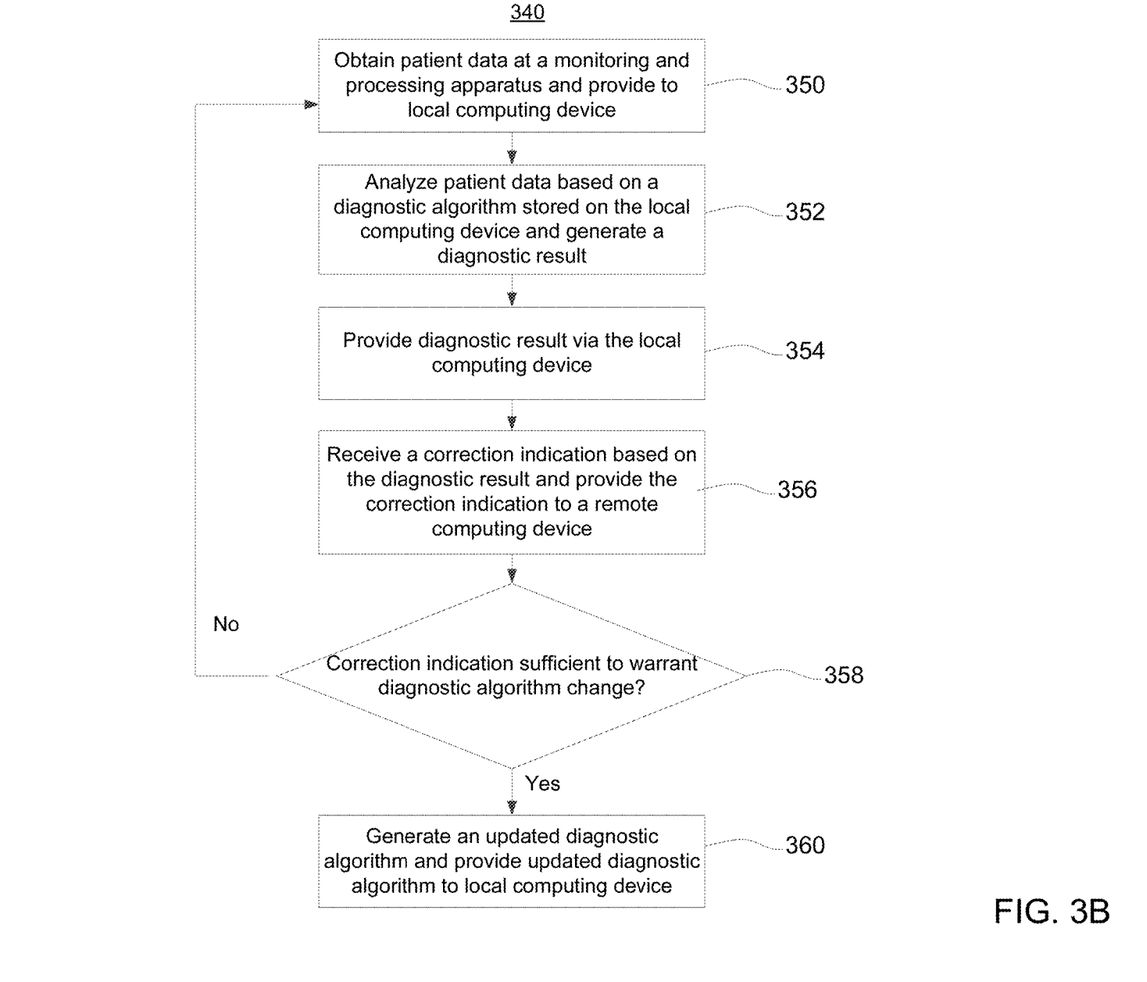
FIG. 3B is a flow chart of another example method of generating an updated diagnostic algorithm

FIG. 3A illustrates a method 300 that includes analyzing patient data based on a diagnostic algorithm that is stored at a monitoring and processing apparatus. FIG. 3B is a flow diagram of a method 340 that includes analyzing patient data based on a diagnostic algorithm that is stored at a local computing device. As methods 300 and 340 are similar, though not the same, overlapping disclosure and examples are omitted. However, it should be understood that description and examples provided with respect to method 300 of FIG. 3A also apply to the method 340 described in FIG. 3B.

At 350 of method 340, patient data may be obtained at a monitoring and processing apparatus. The patient data may be obtained by one or more sensors configured to sense patient biometric data. The patient data may be sampled continuously or at pre-determined or dynamically determined time intervals and may be stored in a memory, such as memory 118 of FIG. 1. The obtained patient data may be transmitted by a monitoring and process apparatus transceiver, such as transceiver 122 of FIG. 1, and may be received by a local computing device such as local computing device 106. The patient data may be transmitted over a local area network 110. According to an embodiment, the patient data may be sampled based on a patient input. A patient input may include an input via a local computing device, a voice command, a gesture, or the like. FIG. 7 shows an example of a gesture based patient input, as described in relation to 310 of method 300.

At 352 of method 340, the patient data may be analyzed at the local computing device. The patient data may be analyzed by a processor, such as processor 204 of FIG. 2. The processor may analyze the patient data based on a diagnostic algorithm that may be stored in the local computing device memory, such as memory 208. The processor may analyze the patient data based on the diagnostic algorithm in any applicable format such as those described in relation to 312 of method 300.

The diagnostic algorithm may include weights that are configured to enable the diagnostic algorithm to determine a diagnostic result. The weights may enable the diagnostic algorithm to match the patient data to a diagnosis and, accordingly, to provide a diagnostic result. The diagnostic algorithm may be pre-installed and/or stored in the local computing device memory at a time of manufacturing or initial configuration of the local computing device. Alternatively, the diagnostic algorithm may be transmitted onto the local computing device as part of an application installation, application update, or diagnostic algorithm download.

At 354 of method 340, one or more diagnostic results, as determined by the local computing device's processor, may be provided to a healthcare professional via the local computing device (e.g., via a user interface 202 FIG. 2). Additionally, patient data and/or a portion or indication of the patient data obtained by the monitoring and processing apparatus at 350 of method 340 may also be provided via the local computing device. FIG. 4 shows an example user interface 202 of a local computing device. Patient data 401 is provided via the user interface 202 and may be displayed along with a diagnostic result 412 as well as one or more alternative diagnoses 414.

At 356 of method 300, the local computing device may receive a correction indication based on a diagnostic result provided at 354. The correction indication may be provided by a healthcare professional or may be automatically determined based on software located at the local computing device. The health care professional or the local computing device software may provide the correction indication based on one or more factors such as, but not limited to, the patient data (e.g., patient data 401 of FIG. 4), patient history, data from an additional device (e.g., a blood pressure cuff, a weight scale, a bracelet or smart watch biometric tracker, a glucose monitor, a CPAP machine or any device which may provide an input concerning the health or biometrics of the patient), and/or patient observation.

The correction indication received at 356 of method 340 may be provided by a touch input, voice command, via an accessory (e.g., keyboard, mouse), a gesture, or the like. As an example, the correction indication may be provided by selecting one of the diagnoses 414 from the user interface 202 of FIG. 4, using a computer mouse.

Figure 6:
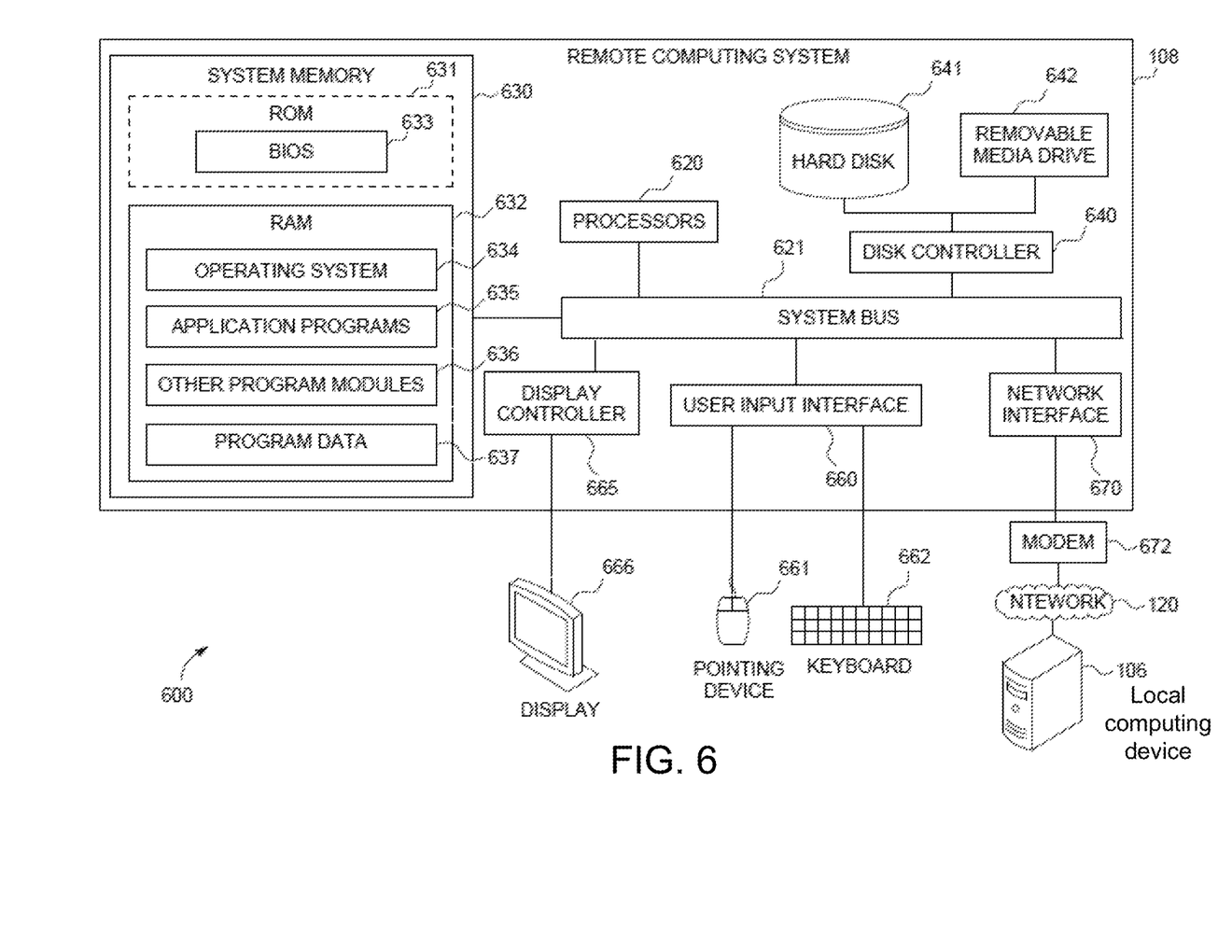
FIG. 6 is a system diagram of an example of a computing environment, which includes the remote computing system shown in FIG. 1.

As shown at 356 of method 340, the correction indication may be provided to a remote computing device such as remote computing device 106 of FIG. 1 and FIG. 6. The correction indication may be provided to the remote computing device via a wide area network such as wide area network 120 of FIG. 1.

At 358 of method 300, the remote computing device may make a determination whether a received correction indication is sufficient to warrant a change to the diagnostic algorithm, as described in relation to 318 of method 300.

If 358 is triggered in the affirmative, 360 of method 340 is performed. At 360, an updated diagnostic algorithm may be generated based at least on the correction indication, as described in relation to 320 of method 300.

An updated diagnostic algorithm, as generated at 360 of method 340, may be stored at a remote computing device memory. According to an embodiment, the updated diagnostic algorithm may be provided to one or more local computing devices. The updated diagnostic algorithm may be provided to the local computing devices when the diagnostic algorithm is updated at 360. Alternatively, the updated diagnostic algorithm may be provided during a software update, application download, or the like.

FIG. 5 is a diagram of an example system 500 that includes multiple patients. For simplified explanatory purposes, a local computing device 106 in FIG. 5 is described as a stationary device, which may be, for example, a healthcare professional computer or a mobile device, which may be, for example, a mobile phone accessible to a health care professional. As described above, local computing devices 106 may be mobile devices or stationary devices. Each local computing device 106 in FIG. 5 may be in communication with attachable monitoring and processing apparatuses 102a and implantable monitoring and processing apparatuses 102b associated with one of the users 502a . . . 502z. For example, information may be sent between each of the local computing devices 106 and associated monitoring and processing apparatuses 102a and 102b via wireless communication channels 520 using any one of various short-range wireless communication protocols. Wireless communication channels 520 may be the same as or similar to the network 110 of FIG. 1.

As shown in FIG. 5, a plurality of attachable monitoring and processing apparatuses 102a (e.g., monitoring and processing apparatus 102 shown in FIG. 1) and/or a plurality of implantable monitoring and processing apparatuses 102b (e.g., implanted subcutaneously within a patient) may be used to monitor patient biometric data of each user 502. The number of attachable monitoring and processing apparatuses 102a and implantable monitoring and processing apparatuses 102b shown in FIG. 5 is merely an example. Any number of attachable monitoring and processing apparatuses 102a and implantable monitoring and processing apparatuses 102b may be used. The location of the attachable monitoring and processing apparatuses 102a and implantable monitoring and processing apparatuses 102b shown in FIG. 5 are also example locations.

In addition to or alternative to the monitoring and processing apparatuses 102a and monitoring and processing apparatuses 102b shown in FIG. 5, an external sensing apparatus 504 may be optionally used to monitor data and may communicate with an associated local computing device 106 via one of the wireless communication channels 520. Although a single external sensing apparatus 504 is shown in FIG. 5, examples include any number of external sensing apparatuses 504 in communication with an associated mobile device.

As shown in FIG. 5, each local computing device 106 may be connected to network 120 (e.g., the Internet) via a wireless communication channel 505. Network 120 is also shown in FIG. 1. A cloud database 512 is an example of a remote computing system 108 of FIG. 1 and is also connected to the network 120 via communication channel 510. The cloud database 512 may be implemented using one or more of the components of the computing environment 600 shown in FIG. 6. In some instances, the cloud database 512 is implemented by a public cloud computing platform (such as Amazon Web Services, or Microsoft Azure), a hybrid cloud computing platform (such as HP Enterprise OneSphere) or private cloud computing platform.

The cloud database 512 may include a machine learning system such as a neural network. The machine learning system may include predetermined or dynamically updated rules and thresholds for updating one or more diagnostic algorithms such as those described with respect to FIGS. 3A and 3B. The cloud database 512 may receive correction indications from local computing devices 106 via wireless communication channel 505 of network 120. As disclosed herein, the cloud database 512 may determine whether one or more correction indications are sufficient to warrant a change in a diagnostic algorithm (e.g., 318 of method 300 and 358 of method 340).

If an updated diagnostic algorithm is generated at the cloud database 512, the updated diagnostic algorithm may be stored in the memory of cloud data base 512 (e.g., system memory 630 of FIG. 6). Alternatively, or additionally, the cloud database 512 may transmit the updated diagnostic algorithm (e.g., via network 120) to one or more local computing devices (e.g., in accordance with process 340) and/or monitoring and processing apparatuses 102 (e.g., in accordance with process 300).

According to an example of the embodiments disclose herein, raw ECG signals from a patient 104 of FIG. 1 may be sensed by sensor 112 of monitoring and processing apparatus 102. The processor 114 of monitoring and processing apparatus 102 may be configured to identify components of the ECG waveform, such as the P wave, the QRS complex, the R wave, the Q wave, the T wave, and the U wave. The components may be identified after initial noise filtration, including removal of baseline wander. The identified components may be analyzed using a diagnostic algorithm stored in memory 118. The diagnostic algorithm may be applied to quantify respective values of the components, such as the respective amplitudes, intervals and/or durations of the P wave, the QRS complex, and the T wave, the R wave and the Q wave, as well as the periods of the P-R interval, the Q-T interval, and the S-T interval. Other parameters that may be quantified may include the slopes of all or some of the waves, the absence or presence of fractionation, and the fractionation value if present.

The diagnostic algorithm may further apply weights to the quantified values, and may analyze the weighted values to generate, as an output, a diagnostic result based on the received ECG signals. The diagnostic result may be provided to a healthcare professional via a computer and the healthcare professional may indicate that the diagnostic result is incorrect based on a review of the raw ECG signal that is also provided to the healthcare professional via the computer. Accordingly, the healthcare professional may provide a correction indication which may provide the correct diagnostic result.

A remote computing device may receive the correction indication and may determine that the number of correction indications received based on the same application of the diagnostic algorithm exceeds a threshold correction indication. Accordingly, the weights contained within the diagnostic algorithm neural network may be updated such that an updated diagnostic algorithm what receives similar ECG signals, as those originally provided in this example, would produce a different diagnostic result. The updated diagnostic algorithm may be provided to one or more local computing devices and/or monitoring and processing apparatuses accordingly.

According to an embodiment, an updated diagnostic algorithm may be provided to a group of monitoring and processing apparatuses (e.g., 320 of process 300) and/or a group of local computing devices (e.g., 360 of process 340). The group of monitoring and processing apparatuses or local computing devices that receives an updated diagnostic algorithm (collectively referred to as distribution group) may be determined based on one or more factors. A distribution group may expand to include additional monitoring and processing apparatuses or local computing devices if an initial distribution of an updated diagnostic algorithm to a smaller distribution group yields a successful result (e.g., lowers the number of correction indications received from within the smaller distribution group). A distribution group may be determined based on the location of corresponding monitoring and processing apparatuses or local computing devices, based on license settings, based on patient volume, based on local regulations and/or requirements, based on random selection, or the like.

According to an example, a remote computing device (e.g., remote computing device 108 of FIG. 1) may generate an updated diagnostic algorithm based on a threshold number of correction indications. The remote computing device may provide the updated diagnostic algorithm to a distribution group of 100 randomly selected local computing devices. The remote computing device may then monitor the correction indications received from those 100 randomly selected local computing devices. Notably, the remote computing device may monitor the specific type of correction indications received from the 100 randomly selected local computing devices and compare them to the correction indications that resulted in the updated diagnostic algorithm. Based on the monitoring, the remote computing device may determine whether the updated diagnostic algorithm lead to more desirable results. For example, the remote computing device may determine whether the updated diagnostic algorithm resulted in fewer correction indications. If the updated diagnostic algorithm leads to more desirable results, the distribution group may be expanded (e.g., to 1000 randomly selected local computing devices). The monitoring and expanding steps may be repeated for multiple iterations.

FIG. 6 is a system diagram of an example of a computing environment 600 in communication with network 120. In some instances, the computing environment 600 is incorporated in a public cloud computing platform (such as Amazon Web Services or Microsoft Azure), a hybrid cloud computing platform (such as HP Enterprise OneSphere) or a private cloud computing platform.

As shown in FIG. 6, computing environment 600 includes remote computing system 108 (hereinafter computer system), which is one example of a computing system upon which embodiments described herein may be implemented.

The remote computing system 108 may, via processors 620, which may include one or more processors, perform various functions. The functions may include analyzing monitored patient biometrics and the associated information and, according to physician-determined or algorithm driven thresholds and parameters, providing (e.g., via display 666) alerts, additional information or instructions. As described in more detail below, the remote computing system 108 may be used to provide (e.g., via display 666) healthcare personnel (e.g., a physician) with a dashboard of patient information, such that such information may enable healthcare personnel to identify and prioritize patients having more critical needs than others.

As shown in FIG. 6, a computing environment 600 may include a communication mechanism such as a bus 621 or other communication mechanism for communicating information within the computing environment 600. The computer system 600 further includes one or more processors 620 coupled with the bus 621 for processing the information. The processors 620 may include one or more CPUs, GPUs, or any other processor known in the art.

The computing environment 600 also includes a system memory 630 coupled to the bus 621 for storing information and instructions to be executed by processors 620. The system memory 630 may include one or more diagnostic algorithms and may include multiple versions of one or more diagnostic algorithms. The system memory 630 may include computer readable storage media in the form of volatile and/or nonvolatile memory, such as read only system memory (ROM) 631 and/or random access memory (RAM) 632. The system memory RAM 632 may include other dynamic storage device(s) (e.g., dynamic RAM, static RAM, and synchronous DRAM). The system memory ROM 631 may include other static storage device(s) (e.g., programmable ROM, erasable PROM, and electrically erasable PROM). In addition, the system memory 630 may be used for storing temporary variables or other intermediate information during the execution of instructions by the processors 620. A basic input/output system 633 (BIOS) may contain routines to transfer information between elements within computer system 610, such as during start-up, that may be stored in system memory ROM 631. RAM 632 may contain data and/or program modules that are immediately accessible to and/or presently being operated on by the processors 620. System memory 630 may additionally include, for example, operating system 634, application programs 635, other program modules 636 and program data 637.

The computing environment 600 also includes a disk controller 640 coupled to the bus 621 to control one or more storage devices for storing information and instructions, such as a magnetic hard disk 641 and a removable media drive 642 (e.g., floppy disk drive, compact disc drive, tape drive, and/or solid state drive). The storage devices may be added to the computer system 610 using an appropriate device interface (e.g., a small computer system interface (SCSI), integrated device electronics (IDE), Universal Serial Bus (USB), or FireWire).

The computing environment 600 may also include a display controller 665 coupled to the bus 621 to control a monitor or display 666, such as a cathode ray tube (CRT) or liquid crystal display (LCD), for displaying information to a computer user. The illustrated computer system 610 includes a user input interface 660 and one or more input devices, such as a keyboard 662 and a pointing device 661, for interacting with a computer user and providing information to the processor 620. The pointing device 661, for example, may be a mouse, a trackball, or a pointing stick for communicating direction information and command selections to the processor 620 and for controlling cursor movement on the display 666. The display 666 may provide a touch screen interface that may allow input to supplement or replace the communication of direction information and command selections by the pointing device 661 and/or keyboard 662.

The computing environment 600 may perform a portion or each of the functions and methods described herein in response to the processors 620 executing one or more sequences of one or more instructions contained in a memory, such as by utilizing one or more diagnostic algorithms in the system memory 630. Such instructions may be read into the system memory 630 from another computer readable medium, such as a hard disk 641 or a removable media drive 64. The hard disk 641 may contain one or more data stores and data files used by embodiments described herein. Data store contents and data files may be encrypted to improve security. The processors 620 may also be employed in a multi-processing arrangement to execute the one or more sequences of instructions contained in system memory 630. In alternative embodiments, hard-wired circuitry may be used in place of or in combination with software instructions. Thus, embodiments are not limited to any specific combination of hardware circuitry and software.

As stated above, the computer system 610 may include at least one computer readable medium or memory for holding instructions programmed according to embodiments described herein and for containing data structures, tables, records, or other data described herein. The term computer readable medium as used herein refers to any non-transitory, tangible medium that participates in providing instructions to the processor 620 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 641 or removable media drive 642. Non-limiting examples of volatile media include dynamic memory, such as system memory 630. Non-limiting examples of transmission media include coaxial cables, copper wire, and fiber optics, including the wires that make up the bus 621. Transmission media may also take the form of acoustic or light waves, such as those generated during radio wave and infrared data communications.

The computing environment 600 may further include a networked environment using logical connections to local computing device 106 and one or more other devices, such as a personal computer (laptop or desktop), mobile devices (e.g., patient mobile devices), a server, a router, a network PC, a peer device or other common network node, and typically includes many or all of the elements described above relative to computer system 610. When used in a networking environment, computer system 610 may include modem 672 for establishing communications over a network 120, such as the Internet. Modem 672 may be connected to system bus 621 via network interface 670, or via another appropriate mechanism.

Network 120, as shown in FIGS. 1 and 6, may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 610 and other computers (e.g., local computing device 106).

Any of the functions and methods described herein can be implemented in a general-purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer-readable media). The results of such processing can be maskworks that are then used in a semiconductor manufacturing process to manufacture a processor which implements features of the disclosure.

Any of the functions and methods described herein can be implemented in a computer program, software, or firmware incorporated in a non-transitory computer-readable storage medium for execution by a general-purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

It should be understood that many variations are possible based on the disclosure herein. Although features and elements are described above in particular combinations, each feature or element can be used alone without the other features and elements or in various combinations with or without other features and elements.

The invention claimed is:

1. A system comprising:
   a first monitoring and processing apparatus comprising:
      a memory configured to store a diagnostic algorithm,
      a sensor configured to sense patient data of a first patient, and
      a processor configured to generate a first diagnostic result based on the patient data and the diagnostic algorithm;

a local computing device comprising a local computing processor and configured to:
  receive the first diagnostic result via a first network,
  receive a correction indication that comprises a correction of the first diagnostic result, the correction indication resulting from a determination that the diagnostic result is incorrect, the correction indication based upon one or more factors comprising (i) the first patient's patient history; (ii) the first patient's patient data; (iii) data regarding the first patient obtained from a medical device; and (iv) observation of the first patient,
  determine whether the correction indication is a sufficient correction indication based upon one or more factors comprising (i) source of the correction indication; (ii) number of similar correction indications; and (iii) frequency of similar correction indications received, and
  transmit the sufficient correction indication via a second network;
a remote computing device configured to:
  generate an updated diagnostic algorithm that is updated based on the sufficient correction indication, and
  transmit the updated diagnostic algorithm via the second network;
and
an initial distribution group of monitoring and processing apparatuses utilized on multiple patients, wherein the updated diagnostic algorithm is generated based upon receiving a number of sufficient correction indications exceeding a threshold number, and wherein the size of the initial distribution group increases based upon the updated diagnostic algorithm reducing the number of sufficient correction indications below the threshold number.

2. The system of claim 1, wherein the diagnostic algorithm comprises a first weight and the updated diagnostic algorithm comprises an updated first weight.

3. The system of claim 1, wherein sensor is configured to sense the patient data using one or more electrodes coupled to the monitoring and processing apparatus.

4. The system of claim 1, wherein the patient data comprises an electrocardiograph (ECG) signal.

5. The system of claim 1, wherein the monitoring and processing apparatus is one of an external apparatus or an implantable apparatus.

6. The system of claim 1, wherein the first network is a local area network (LAN) and the second network is a wide area network (WAN).

7. The system of claim 1, wherein the updated diagnostic algorithm is received by a plurality of second monitoring and processing apparatuses and the plurality of second monitoring and processing apparatuses are selected based on at least one of a location, a predetermined grouping, or a patient-based grouping.

8. A method comprising:
sensing patient data of a first patient at a first monitoring and processing apparatus;
generating a first diagnostic result based on the patient data and a diagnostic algorithm;
transmitting the first diagnostic result via a first network;
receiving an updated diagnostic algorithm from a local computing device via the first network, the updated diagnostic algorithm based at least on a correction indication comprising a correction of the first diagnostic result and provided to the local computing device by a remote computing device via a second a second network the correction indication resulting from a determination that the first diagnostic result is incorrect, the correction indication based upon one or more factors comprising (i) the first patient's patient history; (ii) the first patient's patient data; (iii) data regarding the first patient obtained from a medical device; and (iv) observation of the first patient;
determining whether the correction indication is a sufficient correction indication based upon one or more factors comprising (i) source of the correction indication; (ii) number of similar correction indications; and (iii) frequency of similar correction indications received;
generating a second diagnostic result based on the updated diagnostic algorithm; and,
forming an initial distribution group of monitoring and processing apparatuses for use on multiple patients, wherein the updated diagnostic algorithm is generated based upon receiving a number of sufficient correction indications exceeding a threshold number, and wherein the size of the initial distribution group increases based upon the updated diagnostic algorithm reducing the number of sufficient correction indications below the threshold number.

9. The method of claim 8, wherein the diagnostic algorithm comprises a first weight and the updated diagnostic algorithm comprises an updated first weight.

10. The method of claim 8, wherein sensing patient data at the monitoring device comprises sensing the patient data using one or more electrodes coupled to the monitoring and processing apparatus.

11. The method of claim 8, wherein the patient data comprises an electrocardiograph (ECG) signal.

12. The method of claim 8, wherein the monitoring and processing apparatus is one of an external apparatus or an implantable apparatus.

13. The method of claim 8, wherein the first network is a local area network (LAN) and the second network is a wide area network (WAN).

14. A system comprising:
a first monitoring and processing apparatus comprising:
  a sensor configured to sense patient data of a first patient, and
  a transmitter configured to transmit the patient data via a first network;
a local computing device comprising:
  a memory configured to store a diagnostic algorithm, and
  a processor configured to:
    receive the patient data via the first network,
    generate a first diagnostic result based on the patient data and the diagnostic algorithm,
    receive a correction indication that comprises a correction of the first diagnostic result, the correction indication resulting from a determination that the first diagnostic result is incorrect, the correction indication based upon one or more factors comprising (i) the first patient's patient history; (ii) the first patient's patient data; (iii) data regarding the first patient obtained from a medical device; and (iv) observation of the first patient,
    determine whether the correction indication is a sufficient correction indication based upon one or more factors comprising (i) source of the correction indication; (ii) number of similar correction indications; and (iii) frequency of similar correction indications received, and
transmit the sufficient correction indication via a second network;
a remote computing device configured to:
generate an updated diagnostic algorithm that is updated based on the sufficient correction indication, and
transmit the updated diagnostic algorithm via the second network;
and,
an initial distribution group of monitoring and processing apparatuses utilized on multiple patients, wherein the updated diagnostic algorithm is generated based upon receiving a number of sufficient correction indications exceeding a threshold number, and wherein the size of the initial distribution group increases in the event the updated diagnostic algorithm reduces the number of sufficient correction indications below the threshold number.

* * * * *

UNITED STATES PATENT AND TRADEMARK OFFICE
CERTIFICATE OF CORRECTION

PATENT NO. : 11,534,067 B2
APPLICATION NO. : 16/541772
DATED : December 27, 2022
INVENTOR(S) : Assaf Govari et al.

It is certified that error appears in the above-identified patent and that said Letters Patent is hereby corrected as shown below:

In the Specification
In Column 1, Lines 66-67, delete "may configured" and insert -- may be configured --, therefor.
In Column 2, Line 17, delete "a second a second" and insert -- a second --, therefor.
In Column 12, Line 62, delete "disclose" and insert -- disclosed --, therefor.
In Column 13, Line 31, delete "what" and insert -- which --, therefor.
In Column 15, Line 38, delete "drive 64." and insert -- drive 642. --, therefor.

In the Claims
In Column 18, Line 1, in Claim 8, delete "a second a second" and insert -- a second --, therefor.

Signed and Sealed this
Twelfth Day of September, 2023

Katherine Kelly Vidal
*Director of the United States Patent and Trademark Office*